(12) United States Patent
Kimba et al.

(10) Patent No.: US 9,645,059 B2
(45) Date of Patent: May 9, 2017

(54) SAMPLE INTRODUCTION SYSTEM AND PARTICLE SIZE DISTRIBUTION MEASURING APPARATUS

(71) Applicant: HORIBA, Ltd., Kyoto-shi, Kyoto (JP)

(72) Inventors: Takashi Kimba, Kyoto (JP); Akihiro Katanishi, Kyoto (JP)

(73) Assignee: HORIBA, LTD., Kyoto (JP)

( * ) Notice: Subject to any disclaimer, the term of this patent is extended or adjusted under 35 U.S.C. 154(b) by 0 days.

(21) Appl. No.: 15/152,987

(22) Filed: May 12, 2016

(65) Prior Publication Data
US 2016/0341648 A1 Nov. 24, 2016

(30) Foreign Application Priority Data
May 21, 2015 (JP) ................................. 2015-104025

(51) Int. Cl.
*G01N 15/02* (2006.01)
*G01N 1/38* (2006.01)

(52) U.S. Cl.
CPC ........... *G01N 1/38* (2013.01); *G01N 15/0211* (2013.01)

(58) Field of Classification Search
CPC ............................. G01N 15/0205; G01N 1/38
USPC ....................................................... 356/336
See application file for complete search history.

(56) References Cited

U.S. PATENT DOCUMENTS

| 2009/0068062 A1* | 3/2009 | Jafari | G01N 1/38 422/64 |
| 2010/0285989 A1* | 11/2010 | Huo | C12Q 1/682 506/9 |
| 2011/0020949 A1* | 1/2011 | Sugiyama | B01F 7/161 436/174 |
| 2013/0130369 A1* | 5/2013 | Wilson | B01L 3/5085 435/289.1 |

FOREIGN PATENT DOCUMENTS

JP 2002214114 A 7/2002

* cited by examiner

Primary Examiner — Sunghee Y Gray
(74) Attorney, Agent, or Firm — Lucas & Mercanti, LLP

(57) ABSTRACT

In order to introduce a sample X into a particle size distribution measuring apparatus 200 while neither using a large amount of liquid nor leaving the sample X, a sample introduction system that introduces the sample X into the particle size distribution measuring apparatus 200 that measures the particle size distribution of the sample X is adapted to include: a sample load part 20 that has a load space S into which the sample X is loaded, and a lead-out port 20a adapted to lead out the sample X loaded into the load space S; and a liquid supply mechanism 50 adapted to, into the load space S, supply liquid that is mixed with the sample X and provided in order to measure the particle size distribution. In addition, the sample introduction system is also adapted such that the liquid supplied by the liquid supply mechanism 50 is conducted to the lead-out port 20a while circulating along an inner circumferential surface 24 forming the load space S of the sample load part 20.

9 Claims, 8 Drawing Sheets

SAMPLE INTRODUCTION SYSTEM AND PARTICLE SIZE DISTRIBUTION MEASURING APPARATUS

CROSS REFERENCE TO RELATED APPLICATION

This Application claims the priority of Japanese Patent Application No. JP2015-104025 filed on May. 21, 2015, application which is incorporated herein by reference.

TECHNICAL FIELD

The present invention relates to a sample introduction system adapted to introduce a sample into a particle size distribution measuring apparatus that measures the particle size distribution of the sample.

BACKGROUND ART

As this sort of sample introduction system, as disclosed in Patent Literature 1, there is one configured to have a sample container containing a sample, and tilt the sample container above a particle size distribution measuring apparatus to introduce the sample into the particle size distribution measuring apparatus.

In such a sample introduction system, if the sample is powder or gelatinous material, as illustrated in FIG. 8, it is adapted to, by providing a tilt surface tilting from the sample container toward the particle size distribution measuring apparatus, and tilting the sample container as well as injecting water into the sample container, mix the sample and the water with each other, and slide down the mixture on the tilt surface to flow it into the particle size distribution measuring apparatus.

However, in the above-described configuration, when injecting water into the sample container, the sample may be scattered and remain on the tilt surface. As a result, there occurs a problem that when introducing the next sample, the sample is mixed with the sample remaining on the tilt surface to prevent accurate measurement.

On the other hand, in order to flow the sample into the particle size distribution measuring apparatus without leaving the sample. It is also possible to inject a large amount of water. However, this case is not preferable because water exceeding an acceptable amount may flow into the particle size distribution measuring apparatus.

CITATION LIST

Patent Literature

Patent Literature 1: JP-A2002-214114

SUMMARY OF INVENTION

Technical Problem

Therefore, the present invention is made in order to solve the above-described problems, and a main object thereof is to introduce a sample into a particle size distribution measuring apparatus while neither using a large amount of liquid nor leaving the sample.

Solution to Problem

That is, a sample introduction system according to the present invention is one adapted to introduce a sample into a particle size distribution measuring apparatus that measures the particle size distribution of the sample, and includes: a sample load part that has a load space into which the sample is loaded, and a lead-out port adapted to lead out the sample loaded into the load space; and a liquid supply mechanism adapted to, into the load space, supply liquid that is mixed with the sample and provided in order to measure the particle size distribution. In addition, the sample introduction system is also adapted such that the liquid supplied by the liquid supply mechanism is conducted to the lead-out port while circulating along an inner circumferential surface forming the load space of the sample load part.

Since the sample introduction system described above is configured such that the liquid supplied by the liquid supply mechanism is conducted to the lead-out port while circulating along the inner circumferential surface of the sample load part, even in the case where the supply amount of the liquid is small, the sample loaded into the load space is conducted to the lead-out port while being mixed with the circulating liquid, making it possible to conduct the sample to the particle size distribution measuring apparatus without leaving the sample.

It is preferable that the load space has a diameter reduction part of which the diameter gradually reduces toward the lead-out port.

In such a configuration, since the liquid is conducted to the lead-out port while circulating on the inner circumferential surface forming the diameter reduction part, it is possible to conduct the sample loaded into the load space to the particle size distribution measuring apparatus without leaving the sample.

In order to efficiently conduct the sample to the lead-out port without using a large amount of liquid, it is preferable that the inner circumferential surface is of a rotating body shape of which the central axis is provided along the vertical direction, and the liquid supply mechanism supplies the liquid along a tangential direction to the inner circumferential surface.

In order to flow the liquid along the inner circumferential surface with a simple configuration, the liquid supply mechanism preferably has a liquid supply path that is opened in the inner circumferential surface to communicatively connect to the load space and through which the liquid flows.

In order to more surely introduce the sample into the particle size distribution measuring apparatus without leaving the sample, it is preferable that the liquid supply mechanism has multiple liquid supply paths.

Preferably, the sample introduction system further includes an introduction pipe that is communicatively connected to the lead-out port and adapted to conduct the sample led out of the lead-out port and the liquid led out of the lead-out port to the particle size distribution measuring apparatus, and the supply amount of the liquid to be supplied by the liquid supply mechanism is set such that the liquid flows through the introduction pipe without being interrupted.

Such a configuration makes it possible to prevent the sample from remaining in the introduction pipe, and even in the case where the sample load part is in a place apart from the particle size distribution apparatus, introduce the sample into the particle size distribution measuring apparatus through the introduction pipe without leaving the sample.

In order to prevent the liquid supplied into the load space from being scattered around, preferably, the sample introduction system further includes a scattering prevention member that is provided above the load space to cover at least a part of the load space and prevents the liquid supplied by the liquid supply mechanism from being scattered out of the load space.

A sample such as relatively heavy powder is difficult to flow only by simply circulating the liquid, and therefore in order to conduct such a sample to the particle size distribution measuring apparatus without leaving the sample, it is preferable that the liquid supply mechanism intermittently supplies the liquid into the load space.

Also, a particle size distribution measuring apparatus according to the present invention is one using the sample introduction system described above, and such a particle size distribution measuring apparatus can obtain the above-described working effect.

Advantageous Effects of Invention

The present invention configured as described makes it possible to introduce the sample into the particle size distribution apparatus while neither using a large amount of liquid nor leaving the sample.

DESCRIPTION OF EMBODIMENTS

In the following, one embodiment of a sample introduction system according to the present invention will be described.

A sample introduction system 100 of the present embodiment is one adapted to introduce a sample X into a particle size distribution measuring apparatus 200 that measures the particle size distribution of the sample X.

First, the particle size distribution measuring apparatus 200 will be described. The particle size distribution measuring apparatus 200 is of a so-called diffraction/scattering type adapted to, on the basis of the fact that a light intensity distribution with respect to the spread angle of diffracted/scattered light produced when irradiating particles with light is determined by particle sizes in accordance with MIE scattering theory, measure a particle size distribution by detecting diffracted/scattered light.

Figure 1:
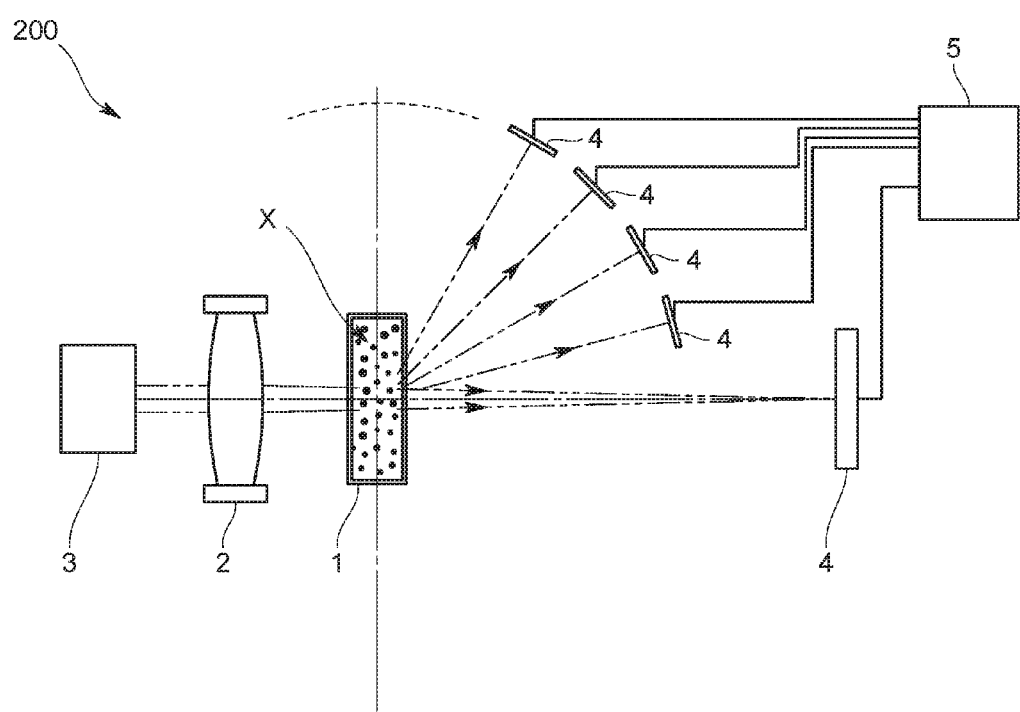
FIG. 1 is a diagram schematically illustrating a particle size distribution measuring apparatus in the present embodiment.

Specifically, as schematically illustrated in FIG. 1, the particle size distribution measuring apparatus 200 includes: a cell 1 adapted to contain the sample X; a laser device as a light source 3 adapted to irradiate the sample X in the cell 1 with laser light through a lens 2; multiple light detectors 4 adapted to detect the light intensities of diffracted/scattered lights produced by the irradiation with the laser light at respective angles within a spread angle; and an operation part 5 adapted to receive light intensity signals outputted from the respective light detectors 4 to calculate the particle size distribution.

In addition, the sample X in the present embodiment is powder, gelatinous material, or solution, and contained in the cell 1 in a state of being dispersed in a solvent (e.g., water or an organic solvent such as ethanol).

Next, the sample introduction system 100 will be described.

Figure 2:
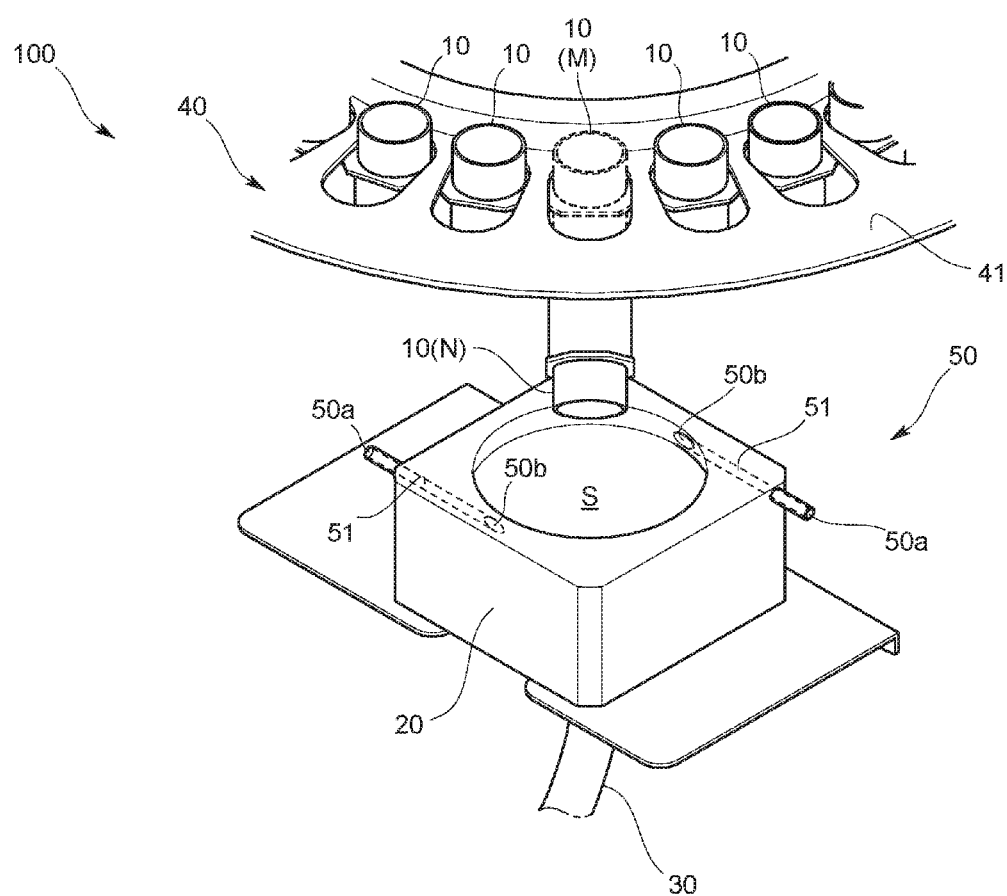
FIG. 2 is a diagram schematically illustrating the configuration of a sample introduction system of the same embodiment.

The sample introduction system 100 is one adapted to automatically introduce the sample X into the above-described particle size distribution measuring apparatus 200, and specifically, as illustrated in FIG. 2, includes: multiple sample containers 10 in which samples X are contained, respectively; a sample load part 20 into which a sample X is loaded from a sample container 10; and an introduction pipe 30 adapted to conduct the sample X loaded in the sample load part 20 to the particle size distribution measuring apparatus 200.

Note that the respective sample containers 10 may be ones that contain mutually different types of samples X or contain mutually the same type of samples X.

Each of the sample containers 10 is a tubular-shaped one of which the upper end is opened and the lower end is closed, and here the multiple sample containers 10 are provided circumferentially arranged mutually at predetermined intervals.

In the present embodiment, each of the sample containers 10 is provided movably between an upright attitude M where a sample X is contained and a tilt attitude N tilting downward from the upright attitude M by a driving mechanism 40.

As illustrated in FIG. 2, the driving mechanism 40 is one having: a holding member 41 that is configured to be rotatable around a predetermined axis as well as holding the above-described multiple sample containers 10; and an unillustrated actuator that rotates the holding member 41 as well as moving a sample container 10 in a predetermined position between the upright attitude M and the tilt attitude N.

This configuration allows the respective sample containers 10 to rotationally move along the circumferential direction, and a sample container 10 in the predetermined position to tilt from the upright attitude M to the tilt attitude N to slide a sample X contained in the sample container 10 downward.

Figure 3:
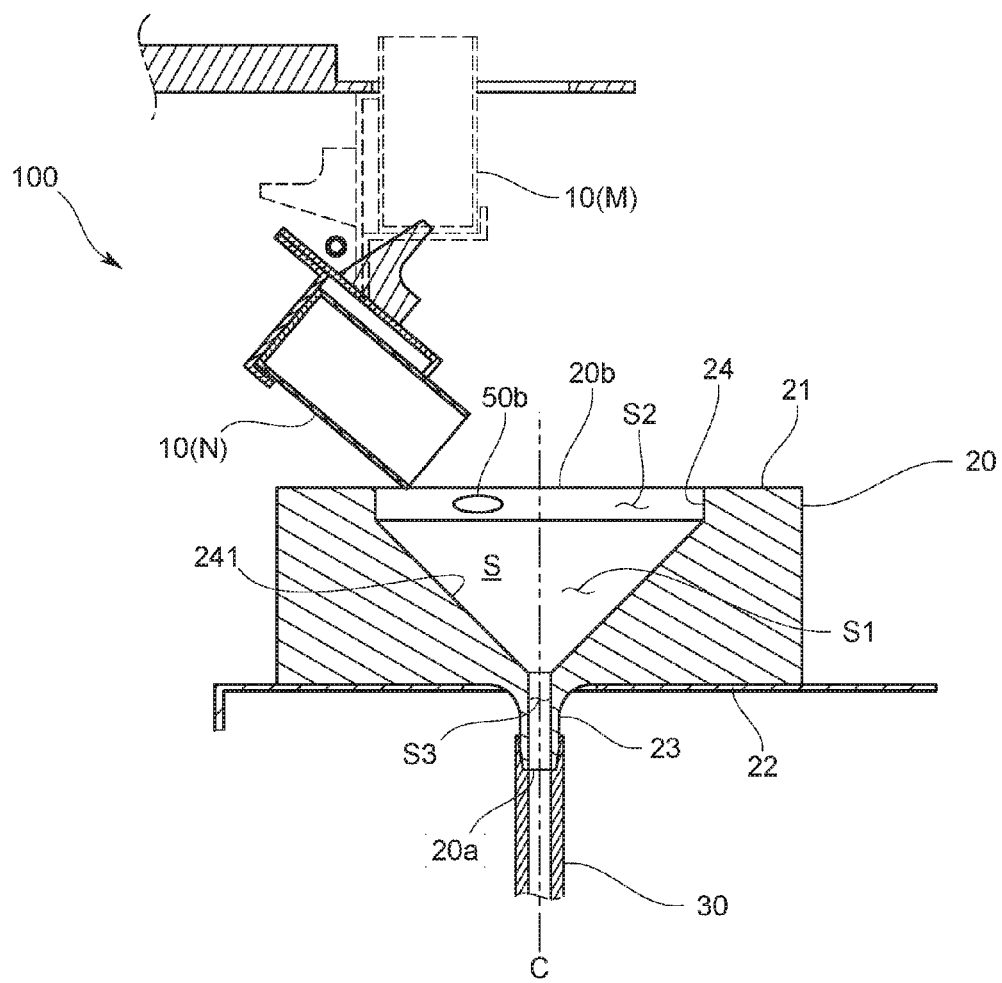
FIG. 3 is a cross-sectional view of a sample load part in the same embodiment.

As illustrated in FIGS. 2 and 3, the sample load part 20 is provided below the sample container 10 in the predetermined position. Also, in the sample load part 20, a load space S into which the sample X slid down from the sample container 10 is loaded, and a lead-out port 20a that is communicatively connected to the load space S and adapted to lead out the loaded sample X are formed.

Specifically, the sample load part 20 has a block body shape, and is formed such that a loading port 20b for loading the sample X is formed in the upper surface 21, the lead-out port 20a is formed in the lower surface 22, and the load space S communicatively connects the loading port 20b and the lead-out port 20a to each other.

In addition, the sample load part 20 in the present embodiment has a protrusion part 23 that protrudes downward from the lower surface 22, and the lead-out port 20a is formed in the fore end surface of the protrusion part 23 as a part of the lower surface 22.

The load space S has a diameter reduction part S1 of which the diameter gradually reduces from the loading port 20b toward the lead-out port 20a, and in the present embodiment, the sample X is loaded onto a tilt surface 241 forming the diameter reduction part S1 among an inner circumferential surface 24 forming the load space S. That is, the sample load part 20 is arranged such that the sample X slid down from the sample container 10 in the predetermined position falls onto the tilt surface 241.

The load space S in the present embodiment is of a rotating body shape, for example, of a funnel shape, and adapted such that the tilt surface 241 is formed over the entire circumference along the circumferential direction.

To give a more detailed description, the load space S has: a large diameter part S2, which communicatively connects the upper end of the diameter reduction part S1 and the loading port 20b to each other and of which the cross section orthogonal to the central axis C is of a uniform circular shape; and a small diameter part S3, which communicatively connects the lower end of the diameter reduction part S1 and the lead-out port 20a to each other and of which the cross-section orthogonal to the central axis C is of a uniform circular shape, and the central axis C is provided along the vertical direction.

The introduction pipe 30 is one adapted to conduct the sample X led out of the lead-out port 20a to the particle size distribution measuring apparatus 200. In addition, here, the introduction pipe 30 is one that is formed so as to make the inside diameter thereof substantially equal to the diameter size of the lead-out port 20a and of which the cross section has a uniform circular shape.

Specifically, the introduction pipe 30 is one of which one end part is attached to the protrusion part 23 and the other end part is connected to, for example, the particle size distribution measuring apparatus 200, and communicatively connects the lead-out port 20a and, for example, a sample loading port of the particle size distribution measuring apparatus 200 for loading the sample X.

Note that the one end part is not necessarily required to be attached to the protrusion part 23, and for example, the introduction pipe 30 may be fixed such that the one end part faces the lead-out port 20a. Also, the other end part is not necessarily required to be connected to the particle size distribution measuring apparatus 200, and for example, the introduction pipe 30 may be fixed such that the other end part faces a mixing part.

In addition, the sample introduction system 100 of the present embodiment is adapted to further include a liquid supply mechanism 50 adapted to supply liquid such as a solvent (e.g., water or an organic solvent such as ethanol), which is mixed with the sample X and then provided in order to measure the particle size distribution, into the load space S.

In the present embodiment, as the liquid, water is used, and the liquid supply mechanism 50 supplies water into the load space S, for example, intermittently at predetermined intervals. A water supply amount to be supplied at a time and the supply interval are predetermined as settings by the below-described supply amount regulating mechanism, and it is here configured to supply water multiple times at intervals of, for example, 1 second such that water supplied at a time is completely discharged from the load space S, and then the next supply is started. By intermittently supply water as described, even in the case where the sample X is one difficult to flow, such as relatively heavy powder, the sample X loaded can be flowed without being left on the inner circumferential surface 24.

Specifically, as illustrated in FIGS. 2 and 3, the liquid supply mechanism 50 has liquid supply paths 51 through which water as the liquid flows, and is configured such that water ejected through the liquid supply paths 51 circulates along the inner circumferential surface 24 forming the load space S, and flows over the entire surface of a part forming the diameter reduction part 51 on the inner circumferential surface 24.

The liquid supply paths 51 are ones adapted to eject water introduced from one end openings 50a from the other end openings 50b, respectively and correspondingly, and the other end openings 50b are formed above a position to which the sample X is loaded.

To give a description more specifically, part of each of the liquid supply paths 51 is provided penetrating through a side wall part of the sample load part 20, and the one end opening 50a of that liquid supply path 51 is provided outside the sample load part 20, whereas the other end opening 50b is formed above the tilt surface 241, i.e., formed in the inner circumferential surface 24 forming the large diameter part S2.

In the present embodiment, in order to circulate water along the inner circumferential surface 24, the liquid supply paths 51 are formed along tangential directions to the inner circumferential surface 24, and here configured to extend in the horizontal direction as well as ejecting water from the other end openings 50b along the horizontal directions, respectively and correspondingly.

In addition, as illustrated in FIG. 2, the liquid supply mechanism 50 has the multiple (e.g., two) liquid supply paths 51 as described above, and the other end openings 50b of the liquid supply paths 51 are formed in the inner circumferential surface 24 at positions symmetrical with respect to the central axis C Further, the sample introduction system 100 of the present embodiment includes the unillustrated supply amount regulating mechanism adapted to regulate the water supply amount to be supplied by the liquid supply mechanism 50.

Note that the present embodiment is adapted to intermittently supply water, and the term "supply amount" refers to a supply amount to be supplied at a time. The supply amount to be supplied at a time may be adapted to be the same amount each time or a different amount depending on how many times the supply has been performed.

The supply amount regulating mechanism has regulators respectively provided in the liquid supply paths 51, such as flow rate regulating valves, and is configured to be able to regulate the supply amount by manually or automatically regulating valve opening levels.

Here, the supply amount regulating mechanism regulates the supply amount such that water does not keep accumulating in the load space S, but flows over the entire inner circumferential surface of the introduction pipe 30 without being interrupted in the introduction pipe 30. Specifically, the supply amount regulating mechanism regulates the supply amount to an amount predetermined on the basis of, for example, the diameter size of the lead-out port 20a, or the inside diameter of the introduction pipe 30.

Specific embodiments of the supply amount regulating mechanism includes one adapted to regulate the supply amount so as to make the supply amount equal to the lead-out amount of the liquid (in this case, water) led out through the lead-out pipe, or regulate the supply amount so as to make the supply amount larger than the lead-out amount.

Note that in the case where the supply amount is larger than the lead-out amount, water accumulates in the load space S, and in this case, the supply amount regulating mechanism is preferably configured to regulate the supply amount so as to make the accumulation height of the liquid accumulating in the load space S equal to or less than a predetermined height lower than the heights of the other end openings 50b of the liquid supply paths 51.

In the sample introduction system 100 according to the present embodiment configured as described, since water supplied into the load space S by the liquid supply mechanism 50 circulates along the inner circumferential surface 24 of the load space S, even in the case where the water supply amount is small, the sample X loaded into the load space S is mixed with water while circulating on the inner circumferential surface 24 together with the water and conducted to the lead-out port 20a. This makes it possible to conduct the sample X to the particle size distribution measuring apparatus 200 while neither using a large amount of water nor leaving the sample.

Also, since the liquid supply mechanism 50 has the multiple liquid supply paths 51, the sample X can be more surely introduced into the particle size distribution measuring apparatus 200 without being left on the inner circumferential surface 24.

Further, since the load space S is formed in a funnel shape, the loading port 20b can be made to have a sufficient size, and therefore the sample X slid down from the sample container 10 can be surely loaded into the load space S without being spilt outside the load space S.

Since the supply amount regulating mechanism regulates the supply amount so as to prevent water from keeping accumulating in the load space S, water supplied by the liquid supply mechanism 50 is ejected to water accumulating in the load space S, and therefore the sample X or water is not scattered.

Also, if water does not flow over the entire inner circumferential surface of the introduction pipe 30 and water flowing through the introduction pipe 30 is interrupted, the sample X may remain attached on the inner circumferential surface of the introduction pipe 30. However, since the supply amount regulating mechanism regulates the supply amount such that water flows over the entire inner circumferential surface of the introduction pipe 30, the sample X can be prevented from being left on the inner surface of the introduction pipe 30. In doing so, even in the case where the particle size distribution measuring apparatus 200 is in a place apart from the lead-out port 20a, the sample X can be introduced into the particle size distribution measuring apparatus 200 through the introduction pipe 30 without being left.

Since the inner circumferential surface 24 of the load space S has a rotating body shape of which the central axis C is provided along the vertical direction, water supplied by the supply mechanism can be surely circulated along the inner circumferential surface 24, and therefore the sample X can be efficiently conducted to the lead-out port 20a by a small amount of water.

Further, since the other end openings 50b of the liquid supply paths 51 are formed above the position on the inner circumferential surface 24 to which the sample X is loaded, and water is ejected from the other end openings 50b along the tangential directions to the inner circumferential surface 24, the water can be prevented from being ejected directly to the sample X, and therefore the sample X can be prevented from being scattered.

Note that the present invention is not limited to the above-described embodiment.

For example, the liquid supply mechanism in the above-described embodiment is configured to eject water along the horizontal direction from the other end openings of the liquid supply paths, but may be configured to eject water upward or downward from the horizontal direction.

Figure 4:
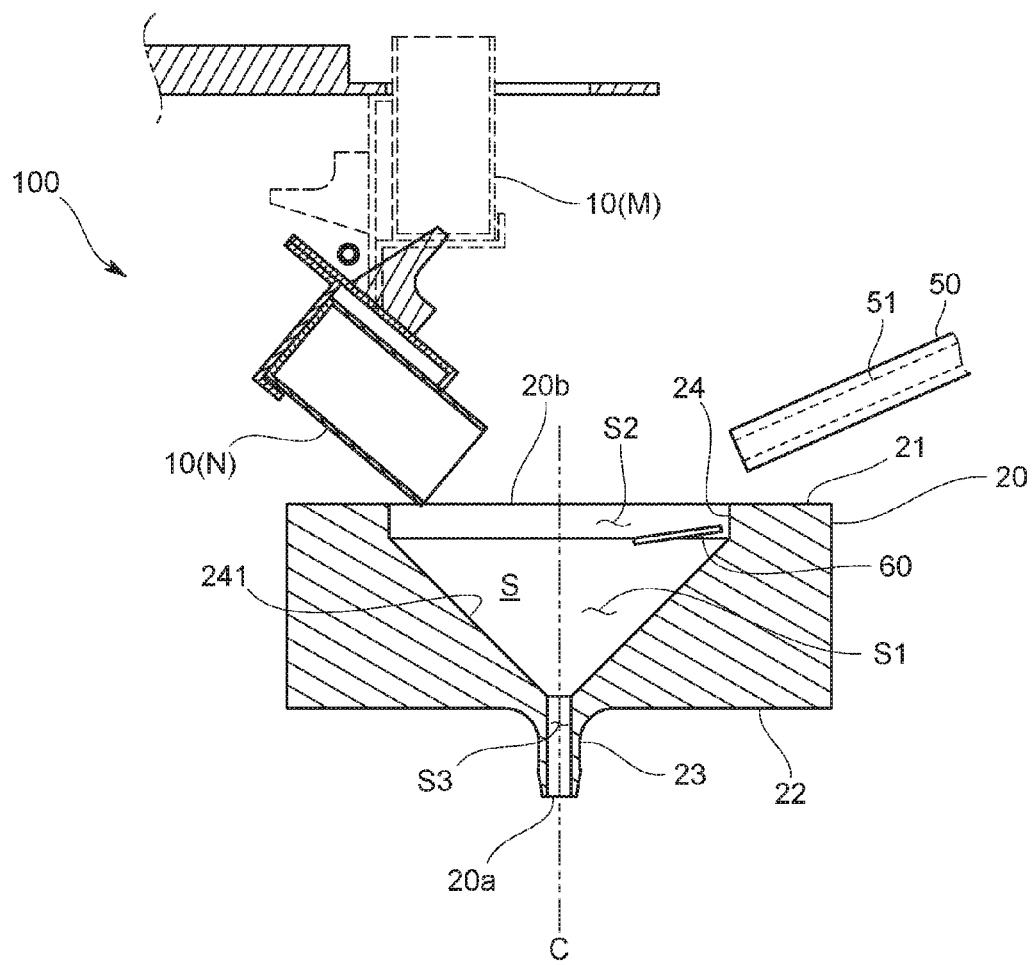
FIG. 4 is a cross-sectional view of a sample load part in a variation.

Also, in the above-described embodiment, the parts of the liquid supply paths are formed penetrating through the sample load part. However, as illustrated in FIG. 4, a liquid supply path 51 may be provided outside the sample load part 20 without communicatively connecting to the lad space S.

More specifically, the liquid supply path 51 is provided such that an opening 50b thereof for ejecting water face the load space S, and ejects water in a direction oblique to the vertically downward direction. In order to surely circulate the water supplied through such a liquid supply path 51 along the inner circumferential surface 24 forming the load space S, a liquid supply mechanism 50 may be configured to further have, for example, a guide member 60 fixed to the inner circumferential surface 24, and circulate the water ejected through the liquid supply path 51 on the inner circumferential surface 24 by flowing the water along the guide member 60.

Further, the liquid supply mechanism is not limited to one adapted to supply water into the load space, but may be one adapted to supply an organic solvent such as ethanol.

The sample load part in the above-described embodiment is one in which the load space of a rotating body shape is formed. However, the load space may be one, for example, of a columnar shape of which the cross section has a polygonal shape or an elliptical shape. In this case, preferably, the load space has, for example, as with the diameter reduction part in the above-described embodiment, a taper part of which the cross section gradually reduces toward the lead-out port.

Also, in the above-described embodiment, the tilt surface forming the diameter reduction part is formed over the entire circumference along the circumferential direction, but may be formed in a part or multiple parts along the circumferential direction.

Further, in the above-described embodiment, the central axis of the load space is provided along the vertical direction, but may be provided obliquely to the vertical direction.

The introduction pipe in the above-described embodiment is configured to make the inside diameter thereof equal to the diameter size of the lead-out port of the sample load part. However, the inside diameter of the introduction pipe can be appropriately changed depending on the liquid supply amount to be supplied by the liquid supply mechanism.

Further, the sample introduction system is not necessarily required to include the introduction pipe. For example, it may be adapted to arrange the particle size distribution measuring apparatus below the lead-out port of the sample load part, and directly conduct a sample from the lead-out port to the particle size distribution measuring apparatus.

Figure 5:
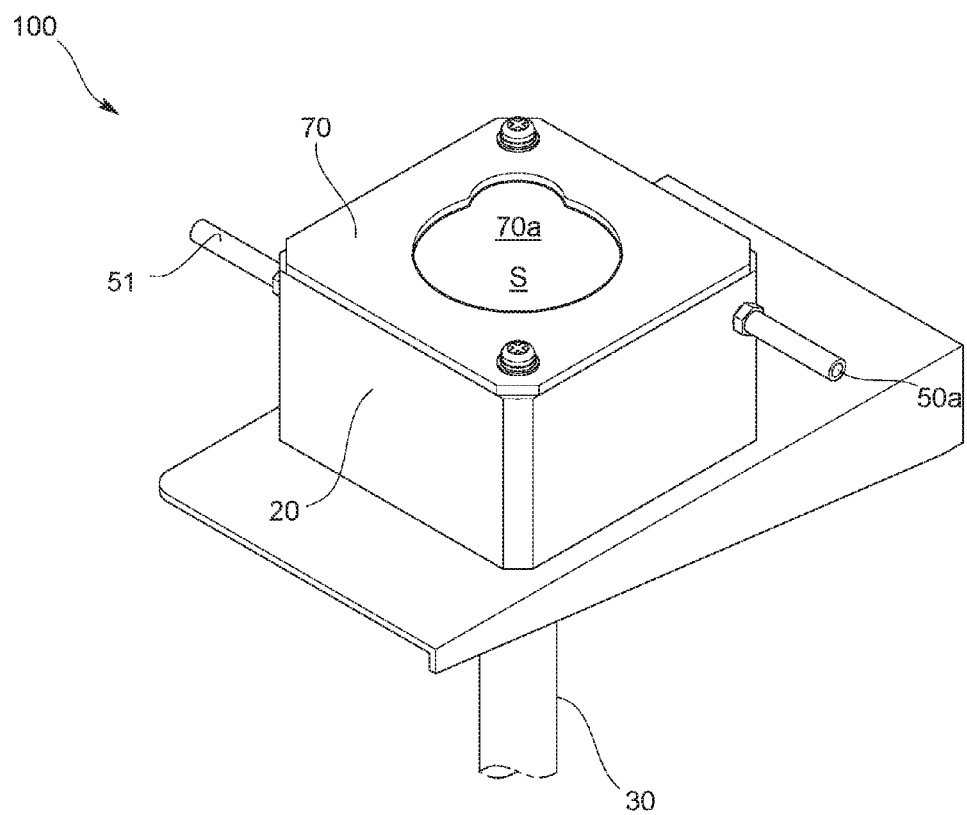
FIG. 5 is a diagram schematically illustrating the configuration of a sample introduction system of another variation.
Figure 6:
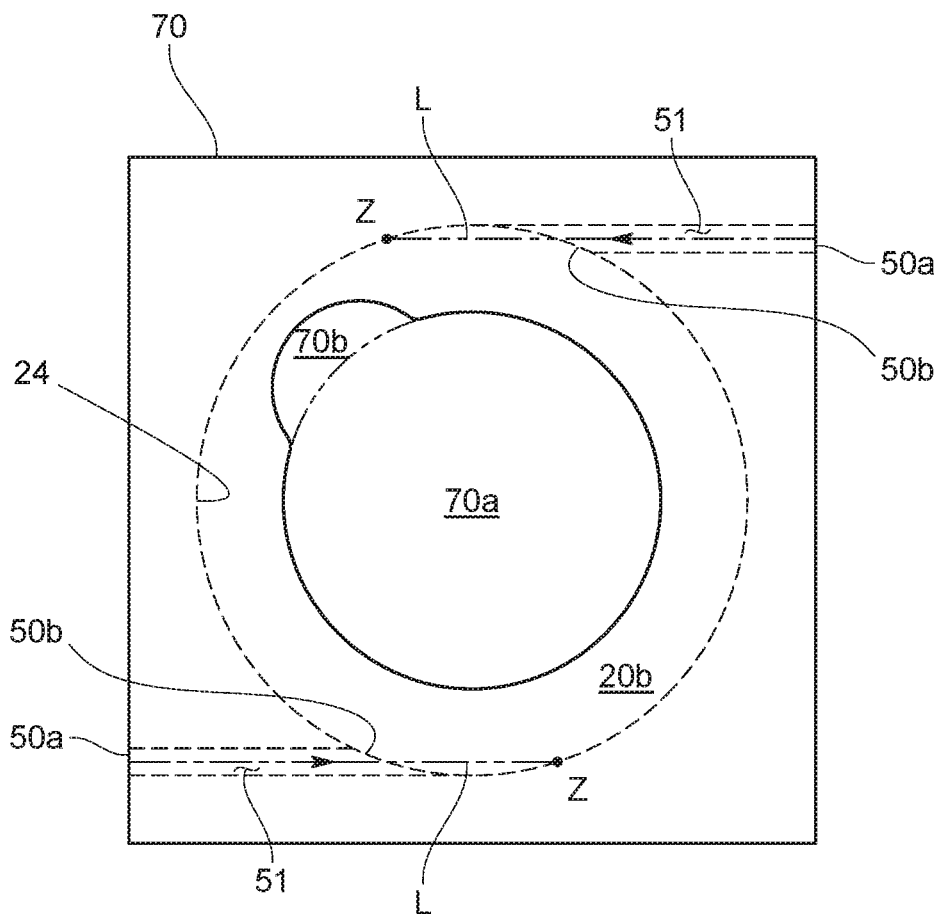
FIG. 6 is a diagram schematically illustrating the configuration of the sample introduction system of the variation.

In addition, as illustrated in FIGS. 5 and 6, the sample introduction system 100 may be one that further includes a scattering prevention member 70 that is provided above the load space S to cover at least part of the load space S, and prevents the liquid supplied by the liquid supply mechanism 50 from being scattered out of the load space S.

Specifically, as illustrated in FIG. 5, the scattering prevention member 70 is attached on the upper surface of the sample load part 20 with, for example, screws, and here a flat plate shaped one in which an opening 70a that faces the loading port 20b and is smaller than the loading port 20b is formed. Note that in the scattering prevention member 70, a cutout part 70b is formed, into which the upper end part of a sample container in the upright attitude gets when the sample container tilts toward the tilt attitude.

As illustrated in FIG. 6, the scattering prevention member 70 is provided above at least parts of the inner circumferential part 24 hit by the liquid supplied through the liquid supply paths 51, and here covers at least parts Z with which the central axes L of the liquid supply paths 51 intersect. In other words, the scattering prevention member 70 is provide so as to cover the parts Z of the inner circumferential surface 24 positioned ahead of the other end openings 50b of the liquid supply paths 51.

The sample introduction system 100 configured as described can prevent the liquid supplied into the load space S from being scattered around.

Figure 7:
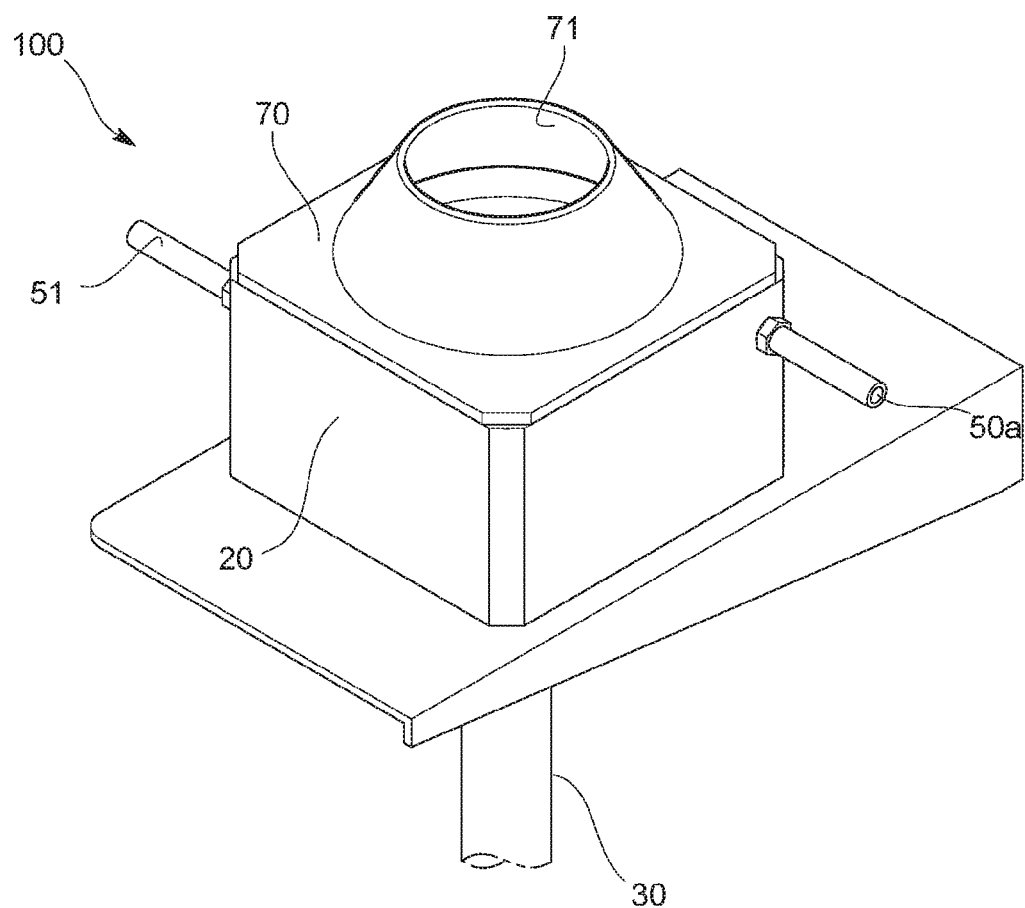
FIG. 7 is a diagram schematically illustrating the configuration of a sample introduction system of still another variation.
Figure 8:
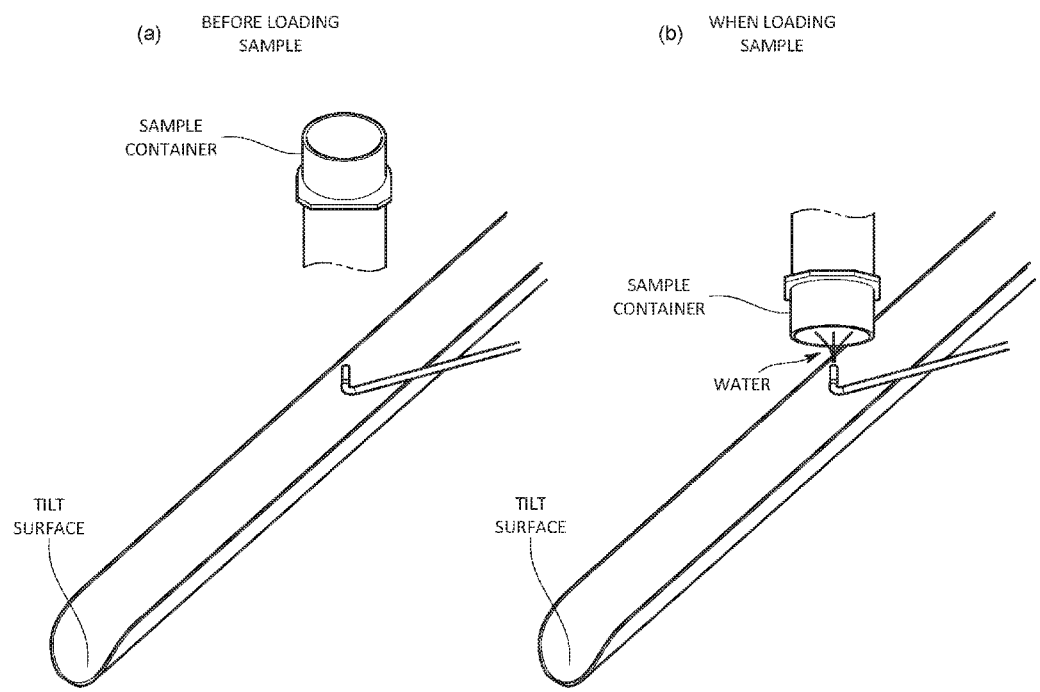
FIG. 8 is a diagram schematically illustrating the configuration of a conventional sample introduction system.

The scattering prevention member 70 is not limited to one having a flat plate shape, but for example, as illustrated in FIG. 7, may be one configured to block at least part of the load space S by a tilt surface 71, such as one having a truncated conical shape. In such a configuration, even if the liquid is scattered and attached on the tilt surface 71, the liquid can be flowed downward along the tilt surface 71.

The particle size distribution measuring apparatus in the above-described embodiment is of a diffraction/scattering type, but may be one of a so-called dynamic light scattering type adapted to measure a particle size distribution on the basis of dynamic light scattering theory.

Besides, it goes without saying that the present invention is not limited to any of the above-described embodiment and variations, but can be variously modified without departing from the scope thereof.

REFERENCE SIGNS LIST

100: Sample introduction system
10: Sample container
20: Sample load part
S: Load space
S1: Diameter reduction part
24: Inner circumferential surface
25: Tilt surface
20a: Lead-out port
C: Central axis
30: Introduction pipe
50: Liquid supply mechanism
51: Liquid supply path

The invention claimed is:

1. A sample introduction system adapted to introduce a sample into a particle size distribution measuring apparatus that measures a particle size distribution of the sample, the sample introduction system comprising:
  a sample load part that has a load space with an inner circumferential surface, into which the sample is loaded, and a lead-out port adapted to lead out the sample loaded into the load space; and
  a liquid supply mechanism adapted to, into the load space, supply liquid that is mixed with the sample and used for measuring the particle size distribution, wherein
  the liquid supply mechanism is configured so that the liquid is ejected from the liquid supply mechanism into the load space, and the liquid ejected into the load space in a direction that causes the ejected liquid to circulate along the inner circumferential surface of the load space toward the lead-out port and thereby forms a vortex.

2. The sample introduction system according to claim 1, wherein
  the load space has a diameter reduction part of which a diameter gradually reduces toward the lead-out port.

3. The sample introduction system according to claim 1, wherein
  the inner circumferential surface is of a rotating body shape of which a central axis is provided along a vertical direction, and
  the liquid supply mechanism supplies the liquid along a tangential direction to the inner circumferential surface.

4. The sample introduction system according to claim 1, wherein
  the liquid supply mechanism has a liquid supply path that is opened in the inner circumferential surface to communicatively connect to the load space and through which the liquid flows.

5. The sample introduction system according to claim 4, wherein
  the liquid supply mechanism has multiple liquid supply paths.

6. The sample introduction system according to claim 1, further comprising
  an introduction pipe that is communicatively connected to the lead-out port and adapted to conduct the sample led out of the lead-out port and the liquid led out of the lead-out port to the particle size distribution measuring apparatus, wherein
  a supply amount of the liquid to be supplied by the liquid supply mechanism is set such that the liquid flows through the introduction pipe without being interrupted.

7. The sample introduction system according to claim 1, further comprising
  a scattering prevention member that is provided above the load space to cover at least a part of the load space and prevents the liquid supplied by the liquid supply mechanism from being scattered out of the load space.

8. The sample introduction system according to claim 1, wherein
  the liquid supply mechanism intermittently supplies the liquid into the load space.

9. A particle size distribution measuring apparatus using the sample introduction system according to claim 1.

* * * * *